(12) United States Patent  (10) Patent No.: US 9,135,708 B2
Ebisawa  (45) Date of Patent: Sep. 15, 2015

(54) GAZE POINT DETECTION METHOD AND GAZE POINT DETECTION DEVICE

(75) Inventor: Yoshinobu Ebisawa, Hamamatsu (JP)

(73) Assignee: NATIONAL UNIVERSITY CORPORATION SHIZUOKA UNIVERSITY (JP)

(*) Notice: Subject to any disclaimer, the term of this patent is extended or adjusted under 35 U.S.C. 154(b) by 162 days.

(21) Appl. No.: 13/814,800

(22) PCT Filed: Aug. 9, 2011

(86) PCT No.: PCT/JP2011/068164
§ 371 (c)(1),
(2), (4) Date: Mar. 26, 2013

(87) PCT Pub. No.: WO2012/020760
PCT Pub. Date: Feb. 16, 2012

(65) Prior Publication Data
US 2013/0188834 A1 Jul. 25, 2013

(30) Foreign Application Priority Data
Aug. 9, 2010 (JP) ................ P2010-178782

(51) Int. Cl.
G06K 9/00 (2006.01)
G06T 7/00 (2006.01)
A61B 3/113 (2006.01)
(52) U.S. Cl.
CPC .......... *G06T 7/004* (2013.01); *A61B 3/113* (2013.01); *G06K 9/00604* (2013.01)
(58) Field of Classification Search
None
See application file for complete search history.

(56) References Cited

U.S. PATENT DOCUMENTS

2010/0208206 A1* 8/2010 Connell, II .............. 351/210

FOREIGN PATENT DOCUMENTS

| JP | 2005-185431 | 7/2005 |
| JP | 2005-198743 | 7/2005 |
| JP | 2005-230049 | 9/2005 |
| JP | 2008-71162 | 3/2008 |

OTHER PUBLICATIONS

Kondou et al, "Easy Eye-Gaze Calibration Using a Moving Visual Target in the Head-Free Remote Eye-Gaze Detection System" VECIMS 2008—IEEE Conference on Virtual Environments, Human-Computer Interfaces, and Measurement Systems, Jul. 14-16, 2008.*

(Continued)

*Primary Examiner* — Chan Park
*Assistant Examiner* — Mai Tran
(74) *Attorney, Agent, or Firm* — Ostrolenk Faber LLP

(57) ABSTRACT

A gaze point detection device 1 comprises two stereo cameras 2a, 2b for acquiring a face image of a subject A, light sources 3a, 3b disposed on the outside of apertures 9a, 9b, a control circuit 4, 5, 6, and an image processor 7. The image processor 7 calculates a vector r from a corneal reflection point to a pupil on a plane perpendicular to reference lines of the stereo cameras 2a, 2b, computes an angle θ of lines of sight of the subject A with respect to the respective reference lines by using a function $f_1$, corrects the function $f_1$ such that directions of lines of sight are closer to each other, and calculates the line of sight directions to detect a gaze point Q on a display screen.

8 Claims, 6 Drawing Sheets

(56) References Cited

OTHER PUBLICATIONS

Kondou et al, Easy Eye-Gaze Calibration Using a Moving Visual Target in the Head-Free Remote Eye-Gaze Detection System, Jul. 2008, VECIMS 2008—IEEE International Conference on Virtual Environments, Human-Computer Interfaces, and Measurement Systems, pp. 1-6.*

Yuki Kondo, et al. "3D Eye-Gaze Detection System Using Stereo-Calibrated Cameras", Proceeding of Vision Engineering Workshop 2009 (ViE2009), Dec. 3, 2009, pp. 343-348 (English Translation).

Yoshinobu Ebisawa, "Development of Video-Based Eye-Gaze Detection System for Human Monitoring", Proceedings of the 9th Takayanagi Kenjiro Memorial Symposium and the 4th International Symposium on Nanovision Science, Oct. 29, 2007, pp. 118-123.

Yuki Kondou and Yoshinobu Ebisawa, "Easy Eye-Gaze Calibration Using a Moving Visual Target in the Head-Free Remote Eye-Gaze Detection System", VECIMS 2008—IEEE International Conference on Virtual Environments, Human-Computer Interfaces, and Measurement Systems, Jul. 14, 2008, pp. 145-150.

International Search Report for PCT/JP2011/068164, date of completion Sep. 2, 2011, dated mailed Sep. 13, 2011.

International Preliminary Report on Patentability (IPRP) for counterpart PCT Application PCT/JP2011/068164, date of mailing of report Mar. 21, 2013.

* cited by examiner

GAZE POINT DETECTION METHOD AND GAZE POINT DETECTION DEVICE

CROSS-REFERENCE TO RELATED APPLICATIONS

The present application is a 35 U.S.C. §§371 national phase conversion of PCT/JP2011/068164, filed Aug. 9, 2011, which claims priority of Japanese Patent Application No. 2010-178782, filed Aug. 9, 2010, the contents of which are incorporated herein by reference. The PCT International Application was published in the Japanese language.

TECHNICAL FIELD

The present invention relates to a gaze point detection method and gaze point detection device for detecting a gaze point of a subject on a predetermined plane according to an image of the subject.

BACKGROUND ART

Devices for detecting a line of sight or gaze point of a test subject in a noncontact manner have conventionally been regarded as important in the field of human interactions. High-precision line of sight detection techniques, if put into practice, can be employed for various uses such as monitoring drivers, inspecting degrees of interest in products, and aiding severely disabled people to input data to personal computers, for example.

Line of sight detection methods disclosed in the following Patent Literatures 1 and 2 make a test subject gaze at both a camera whose position has been known and one point whose position has been known on a display screen, so as to correct a function for calculating a line of sight direction of the test subject from the distance |r| between the center of a pupil and a corneal reflection point, and detect the line of sight direction by using thus corrected function. Such a line of sight detection method can detect a line of sight highly accurately even when the head of the test subject moves. The line of sight detection method disclosed in the following Patent Literature 3 is a method for detecting lines of sight of both eyes at the same time by using two cameras. It is also necessary for this method to make the test subject see a specified point in order to calibrate results of the line of sight detection.

CITATION LIST

Patent Literature

Patent Literature 1: Japanese Patent Application Laid-Open No. 2005-185431
Patent Literature 2: Japanese Patent Application Laid-Open No. 2005-230049
Patent Literature 3: Japanese Patent Application Laid-Open No. 2005-198743

SUMMARY OF INVENTION

Technical Problem

However, correcting results of line of sight detection by making a test subject see a specified point increases the burden on the test subject. When infants, disabled people, autistic patients, and the like are concerned, they may fail to keep their concentration, and some of them have lowered the accuracy in line of sight calibration.

In view of such a problem, it is an object of the present invention to provide a gaze point detection method and gaze point detection device which enables high-precision gaze point detection, while reducing the burden on a test subject, no matter who the subject is.

Solution to Problem

The gaze point detection method in accordance with one aspect of the present invention comprises a face image production step of producing a face image of a subject as a bright pupil image and a dark pupil image by using at least two cameras and a light source disposed on the outside of apertures of the at least two cameras; a vector calculation step of calculating a vector r from a corneal reflection point of the subject to a pupil thereof on a plane perpendicular to a reference line connecting the camera and the pupil according to the face image obtained by each of the at least two cameras; a line of sight direction calculation step of calculating respective angles θ of lines of sight of the subject with respect to the reference lines of the at least two cameras according to the vectors r corresponding to the at least two cameras from the following expression (1):

$$\theta = f(|r|) \tag{1}$$

by using a function f; a parameter correction step of correcting the function f such that the directions of lines of sight calculated so as to correspond to the at least two cameras are closer to each other; and a gaze point detection step of calculating the directions of lines of sight according to the expression (1) by using the function f corrected by the parameter correction step and determining an intersection of the lines of sight on a predetermined plane, so as to detect a gaze point of the subject on the predetermined plane.

The gaze point detection device in accordance with another aspect of the present invention is a gaze point detection device for detecting a gaze point of a subject on a predetermined plane according to a face image of the subject, the device comprising at least two cameras for acquiring the face image of the subject; a light source disposed on the outside of apertures of the at least two cameras; a control circuit for controlling the cameras and light source; and an image processing unit for processing image signals issued from the at least two cameras; wherein the control circuit performs such control as to produce the face image of the subject as a bright pupil image and a dark pupil image; wherein the image processing unit calculates a vector r from a corneal reflection point of the subject to a pupil thereof on a plane perpendicular to a reference line connecting the camera and the pupil according to the face image obtained by each of the at least two cameras, calculates respective angles θ of lines of sight of the subject with respect to the reference lines of the at least two cameras according to the vectors r corresponding to the at least two cameras from the following expression (1):

$$\theta = f(|r|) \tag{1}$$

by using a function f, corrects the function f such that the directions of lines of sight calculated so as to correspond to the at least two cameras are closer to each other, and calculates the directions of lines of sight according to the expression (1) by using the corrected function f and determines an intersection of the lines of sight on a predetermined plane, so as to detect a gaze point of the subject on the predetermined plane.

Thus constructed gaze point detection method and gaze point detection device produce face images of a subject as bright and dark pupil images by at least two cameras and a light source on the outside of their apertures, calculate a vector r from a corneal reflection point of the subject to a pupil thereof according to each face image, and apply the respective vectors r to a function f, so as to calculate respective angles θ of lines of sight of the subject with respect to the reference lines. Further, they correct the function f such that thus calculated directions of lines of sight are closer to each other, calculate the directions of lines of sight by using thus corrected function f, and detect a gaze point on a predetermined plane according to the directions of lines of sight. This automatically corrects the function for computing the line of sight directions without the subject recognizing it and thus enables high-precision gaze point detection while reducing the burden on the subject.

Advantageous Effects of Invention

The gaze point detection method or the gaze point detection device in accordance with one aspect of the present invention enables high-precision gaze point detection, while reducing the burden on a test subject, no matter who the subject is.

DESCRIPTION OF EMBODIMENTS

In the following, preferred embodiments of the gaze point detection method and gaze point detection device in accordance with the present invention will be explained in detail with reference to the drawings. In the explanation of the drawings, the same or equivalent parts will be referred to with the same signs while omitting their overlapping descriptions.

Structure of the Gaze Point Detection Device

First, the structure of a gaze point detection device for carrying out the gaze point detection device in accordance with the present invention will be explained with reference to the drawings. The gaze point detection device of the present invention is a device for detecting a gaze point on a monitor screen of an information processing terminal such as a personal computer according to a face image of a subject.

Figure 1:
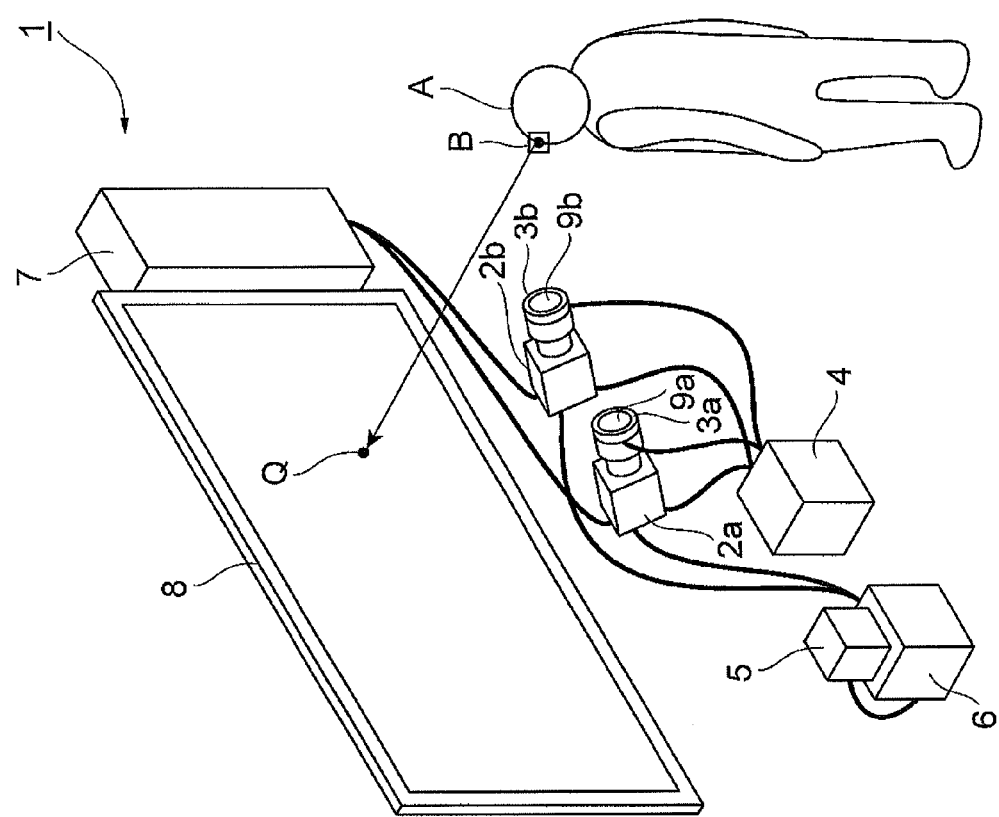
FIG. 1 is a perspective view illustrating a gaze point detection device which is a preferred embodiment of the present invention.

FIG. 1 is a perspective view illustrating a gaze point detection device 1 which is a preferred embodiment of the present invention. As illustrated in this drawing, the gaze point detection device 1 comprises two stereo cameras 2a, 2b for capturing face images of a subject A, light sources 3a, 3b disposed on the outside of respective imaging lenses at apertures of the stereo cameras 2a, 2b, a light emission circuit (control circuit) 4 for feeding the light sources 3a, 3b, a synchronization signal generator (control circuit) 5 for generating synchronization signals to be fed to the stereo cameras 2a, 2b, a delay circuit (control circuit) 6 for delaying the synchronization signals, an image processor (image processing unit) 7 such as a personal computer for processing image signals produced by the stereo cameras 2a, 2b, and a display device 8 arranged so as to face the subject A above the stereo cameras 2a, 2b and connected to the image processor 7. The light emission circuit 4, synchronization signal generator 5, and delay circuit 6 constitute a control circuit for controlling operations of the stereo cameras 2a, 2b and light sources 3a, 3b.

The stereo cameras 2a, 2b capture images of the facial surface of the subject A, so as to produce image data. Employed as the stereo cameras 2a, 2b are cameras of the NTSC system, which is one of interlaced scanning systems. In the NTSC system, 30 frames of image data, each of which is constructed by an odd field composed of odd-numbered horizontal pixel lines and an even field composed of even-numbered horizontal pixel lines excluding the odd-numbered horizontal pixel lines, are obtained in one second by alternately capturing odd and even fields at intervals of 1/60 second. Specifically, within one frame, pixel lines in the odd- and even fields align alternately with each other.

One stereo camera 2a is fed with a vertical synchronization signal (VD signal) from the synchronization signal generator 5, while the other stereo camera 2b is fed with a vertical synchronization signal (VD signal) delayed through the delay circuit 6 from the synchronization signal generator 5, whereby the two stereo cameras 2a, 2b have respective capture timings shifted from each other.

Figure 2:
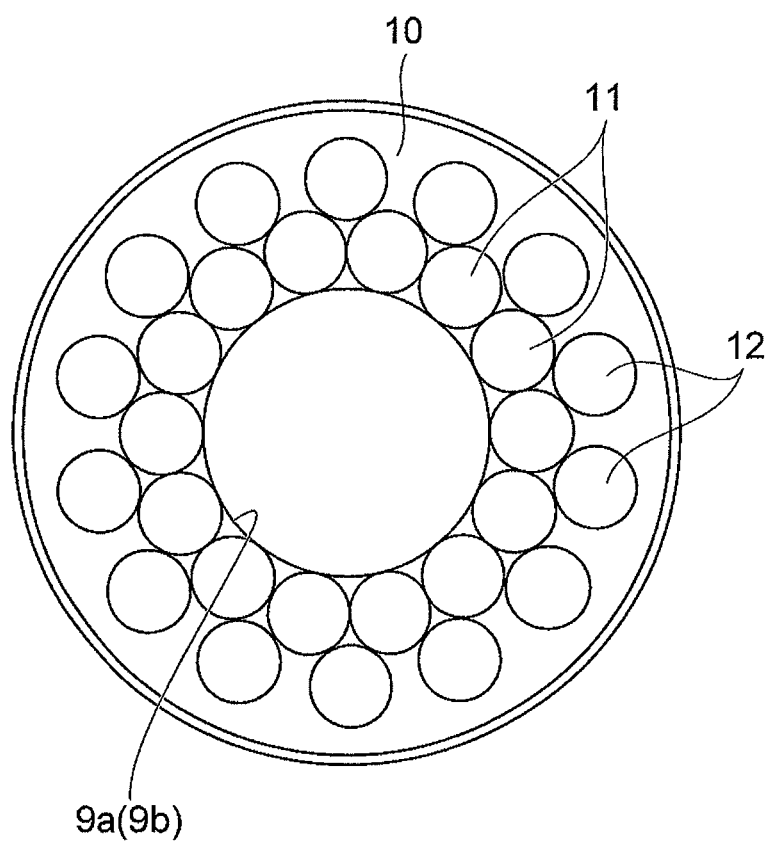
FIG. 2 is a plan view of a light source attached to an aperture of a stereo camera of FIG. 1.

The light sources 3a, 3b are fixed to the outside of circular apertures 9a, 9b containing objective lenses of the stereo cameras 2a, 2b, respectively. FIG. 2 is a plan view of each of the light sources 3a, 3b. Each of the light sources 3a, 3b is used for illuminating the face of the subject A with illumination light and has a structure in which a plurality of two kinds of light-emitting elements 11, 12 are embedded in a ring-shaped base 10. The light-emitting elements 11, each of which is a semiconductor light-emitting element (LED) whose output light has a center wavelength of 850 nm, are arranged like a ring at equally-spaced intervals along edges of the aperture 9a, 9b on the base 10. On the other hand, the light-emitting elements 12, each of which is a semiconductor light-emitting element whose output light has a center wavelength of 950 nm, are arranged at equally-spaced intervals like a ring adjacent to the light-emitting element 11 on the outside thereof on the base 10. That is, the light-emitting elements 12 are configured such as to be distanced more than the light-emitting elements 11 from the optical axis of the camera 2a, 2b. Here, the light-emitting elements 11, 12 are disposed on the base 10 so as to emit the illumination light along the optical axis of the camera 2a, 2b.

The light emission circuit 4 makes it possible to control light emission timings of the light-emitting elements 11, 12 independently of each other. Specifically, the light emission timings are controlled such that the light-emitting elements 11, 12 alternately emit light in response to shutter timings of the cameras 2a, 2b in synchronization with the VD signals issued from the synchronization signal generator 5.

Thus constructed control circuit operates such that a left or right eyeball B of the subject A produces a bright pupil image when illuminated with illumination light from the light-emitting elements 11 of the light source 3a, and a dark bright pupil image when illuminated with illumination light from the light-emitting element 12. This is because of a property that the pupil looks brighter when receiving illumination light having a wavelength shorter than 900 nm than when receiving illumination light having a wavelength longer than 900 nm, and darker when the illumination light to the eyeball B is incident thereon from a position located farther from the optical axis of the camera. As a result, bright and dark pupil images are respectively reflected in the odd and even fields produced by the stereo cameras 2a, 2b.

The image processor 7 processes the image data issued from the two stereo cameras 2a, 2b. Specifically, the image processor 7 separates one frame of image data issued from the stereo cameras 2a, 2b into odd and even fields. For example, the image data of the odd field (odd-number image data) constitutes a bright pupil image, while the image data of the even field (even-number image data) constitutes a dark pupil image. Since such image data has effective pixels in the odd or even field alone, the image processor 7 embeds an average luminance of adjacent lines of effective pixels into a pixel value between the lines, so as to produce bright pupil image data and dark pupil image data.

Further, the image processor 7 repeatedly detects the left and right pupils of the subject A by using the bright pupil image data and dark pupil image data. That is, it produces a difference image between the bright pupil image data and dark pupil image data, sets a window according to the position of the pupil detected by the previous pupil detection processing, and searches for the pupil within the area of the window. Specifically, the image processor 7 binarizes the difference image according to a threshold determined by a percentile method, then eliminates isolated points, performs labeling, and selects pupil candidates from connected components of the labeled pixels according to form parameters such as pupil-like areas, sizes, area ratios, squareness, and pupil characteristic amounts. Further, from connected components of the selected pupil candidates, it determines those in which two pupil candidates have a predetermined relationship therebetween as left and right pupils and computes center coordinates of the left and right pupils in the image data.

The image processor 7 also detects the positions of left and right corneal reflection points of the subject A from the bright pupil image data and dark pupil image data. That is, it sets a window centered at each of the detected pupil, produces image data in which only the window area has a higher resolution, and detects corneal reflection from the image data. Specifically, it determines a binarization threshold by a percentile method, produces a binarized image from thus obtained image, performs labeling, and selects a part having a predetermined area or less. Here, the image processor 7 provides center coordinates of the selected part with a separability filter, so as to obtain a characteristic amount in which separability is multiplied by luminance, and determines that there is no corneal reflection when the resulting amount is a predetermined value or less. The image processor 7 further calculates the amount of movement of corneal reflection from bright pupil image data and dark pupil image data, and takes the amount of movement as a difference position correction amount. Then, the image processor 7 shifts the bright pupil image data and dark pupil image data with respect to each other by the difference position correction amount so that their corneal reflection positions coincide with each other, sums the luminance values of the image data, and determines the luminance gravity center coordinates as corneal reflection coordinates.

From the pupil center coordinates detected on the basis of the image data issued from the two stereo cameras 2a, 2b, the image processor 7 calculates three-dimensional positions of the left and right pupils of the subject A. Here, the image processor 7 measures three-dimensional coordinates of the left and right pupils by a stereo method. The stereo method is a method which measures in advance internal parameters such as focal lengths of lenses, image centers, and pixel sizes in the cameras and external parameters such as positions and postures of the cameras and then, according to coordinates of points in images of the subject captured by a plurality of stereo cameras, determines positions of the points in a space by using the internal and external parameters.

Figure 3:
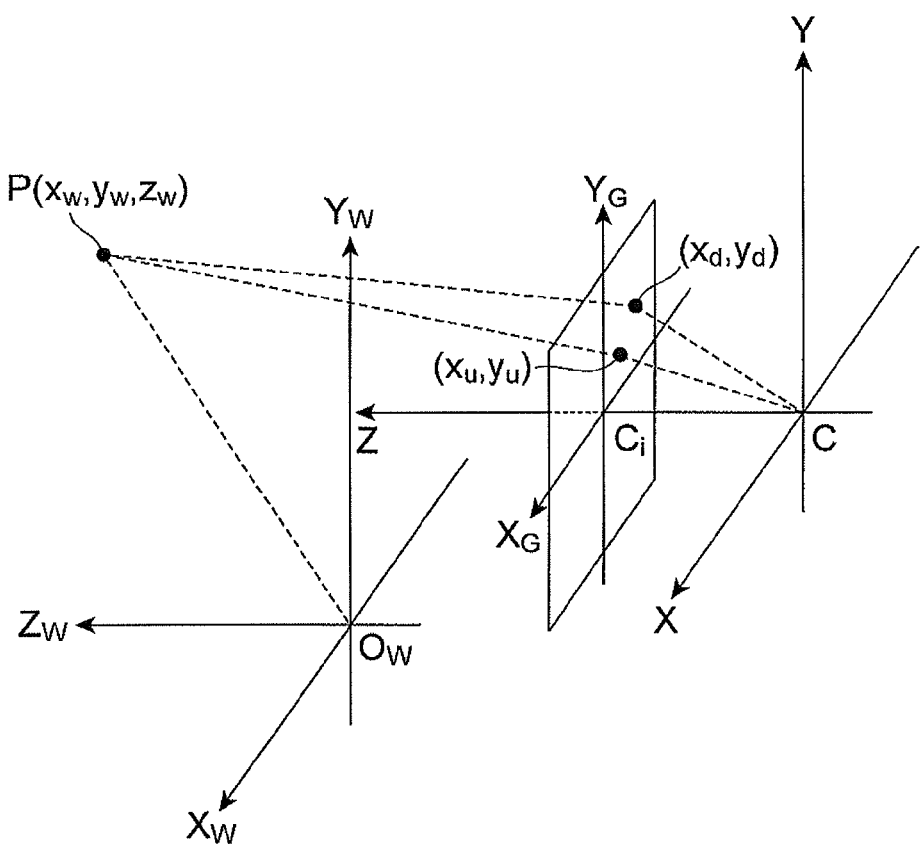
FIG. 3 is a diagram illustrating a positional relationship of coordinate systems set in the gaze point detection device of FIG. 1.

When calculating the three-dimensional coordinates of the pupils by using the stereo method, the image processor 7 employs a coordinate system such as the one illustrated in FIG. 3. The depicted world coordinate system $(X_w, Y_w, Z_w)$ is a coordinate system in which an origin $O_w$ shared by the two stereo cameras 2a, 2b located at the center of the screen of the display device 8, for example; the camera coordinate system (X, Y, Z) is a coordinate system whose origin C is the optical center of the cameras 2a, 2b, while the Z axis is parallel to an optical axis drawn perpendicular to the image plane from the optical center; and the image coordinate system $(X_G, Y_G)$ is a coordinate system made parallel to the XY plane along the image plane where imaging devices are placed, while the intersection (image center) between the optical axis and the image plane is taken as its origin Ci. Assuming a point P to have target coordinates, a projected point $(X_d, Y_d)$ to the image coordinate system when using the cameras 2a, 2b shifts from an ideal projected point $(X_u, Y_u)$ under distortions of images. Hence, for accurately performing the three-dimensional positional measurement using the stereo method, calibration data in which the correspondence between the world and image coordinates of the target point P is recorded must be acquired beforehand. As examples of such calibration data, translation vectors and rotation matrices of the camera coordinate system with respect to the world coordinates as external parameters and focal lengths, image center coordinates, scale factors, lens distortion coefficients, distances between imaging devices, and the like as internal parameters are acquired beforehand and stored in the image processor 7.

Then, while referring to the calibration data, the image processor 7 acquires relational expressions between the pupil center coordinates in the image coordinate system detected on the basis of the output data from the two stereo cameras 2a, 2b and the pupil center coordinates in the world coordinate system. Subsequently, the image processor 7 determines the three-dimensional positional coordinates of the pupils of the subject A in the world coordinate system from two relational expressions. Similarly, the image processor 7 can determine the three-dimensional positions of the left and right pupils of the subject A.

By using the detected positions of the left and right corneal reflection points and left and right pupil centers of the subject A, the image processor 7 detects a gaze point of the subject on the display device 8. In the following, a gaze point detection procedure by the image processor 7 will be explained with reference to FIGS. 4 and 5.

Gaze Point Detection Procedure by an Automatic Calibration Method

Figure 4:
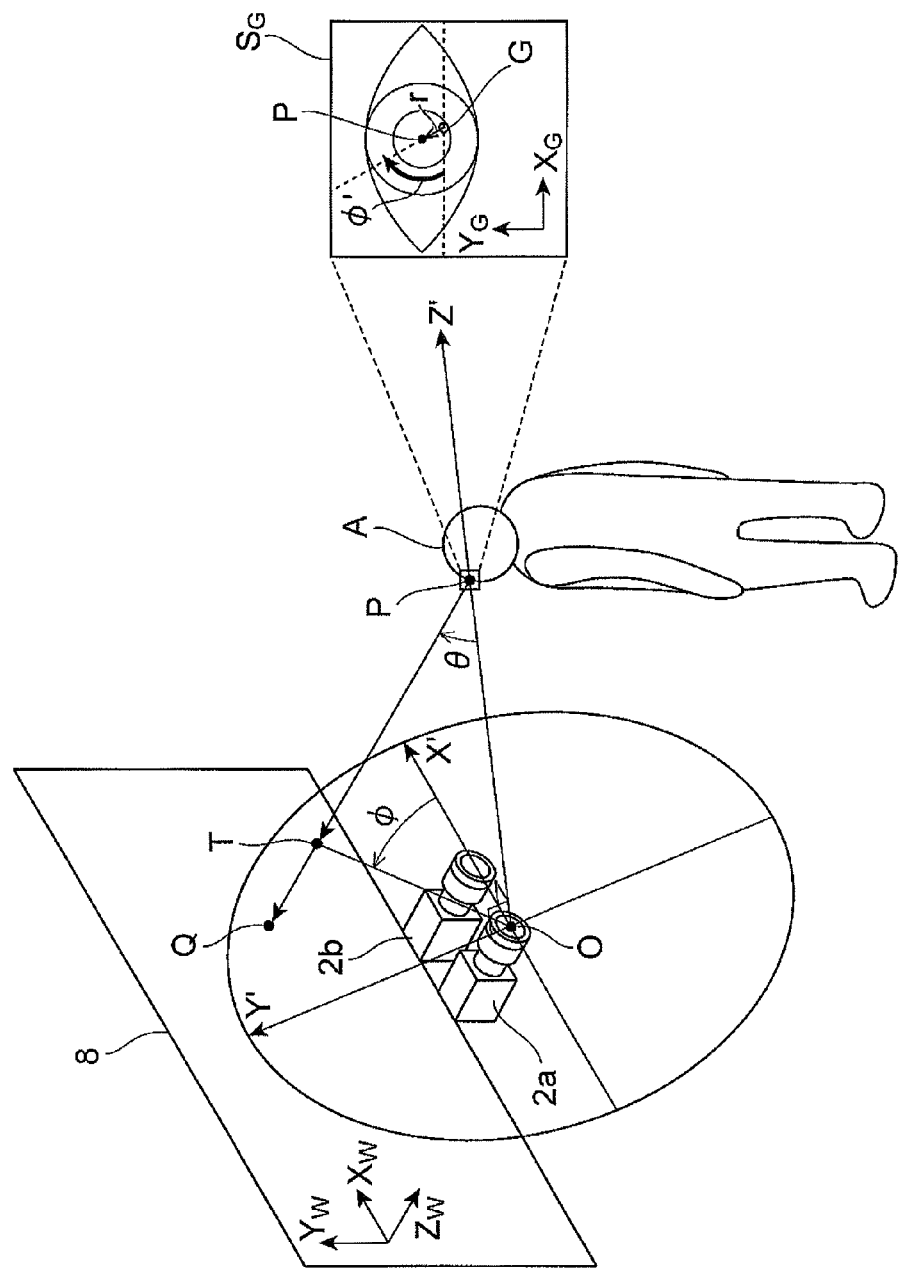
FIG. 4 is a diagram for explaining a gaze point detection procedure by the gaze point detection device of FIG. 1.

Here, as illustrated in FIG. 4, on the basis of the detected three-dimensional pupil position P, the center of the aperture 9a, 9b of the camera 2a, 2b is taken as the origin O, and a virtual gaze point plane X'-Y' to which a reference line OP connecting the origin O and the pupil P is normal is set.

First, the image processor 7 computes a vector $r_0$ from a corneal reflection point G to the pupil center P on an image plane $S_G$. Then, it transforms the vector $r_0$ into a vector r converted into an actual size by using the magnification ratio of the camera determined from the distance OP (vector calculation step). Here, assuming each camera 2a, 2b to be a pinhole model, the corneal reflection point G and the pupil center P are supposed to be located on a plane parallel to the virtual gaze point plane X'-Y'. That is, the image processor 7 computes relative coordinates of the pupil center P and corneal reflection point G as the vector r on a plane which is parallel to the virtual gaze point plane and includes the three-dimensional coordinates of the pupil P.

Thereafter, concerning the gaze point T of the subject A on the virtual gaze point plane, the image processor 7 determines the gradient φ of the line OT with respect to the horizontal axis X' as the one equal to the gradient φ' of the vector r with respect to the horizontal axis $X_G$ on the image plane. Further, by employing a function $f_1$ using a coefficient k, the image processor 7 calculates the angle θ between a line of sight vector of the subject A, i.e., a vector PT connecting the pupil center P and the gaze point T, and the reference line OP according to the following expression (3):

$$\theta = f_1(|r|) = k \times |r| \quad (3)$$

(line of sight direction calculation step).

Here, a preset initial value is employed as the coefficient k. Such calculations of the angles φ, θ are performed by assuming that the vector r on the plane where the pupil center P is located, when expanded on the virtual gaze point plane, corresponds to the gaze point of the subject A as it is. More specifically, the angle θ of the line of sight PT of the subject A with respect to the reference line OP is assumed to have a linear relationship with the distance |r| between the pupil center and the corneal reflection. However, the above-mentioned coefficient k varies depending on the subject A and left and right eyeballs and thus must be calibrated.

Hence, the image processor 7 corrects the coefficient k as follows (parameter correction step). The coefficient k is corrected by determining a coefficient k for each frame on the basis of 100 continuous frames of image data and taking their average as the final coefficient k.

Figure 5:
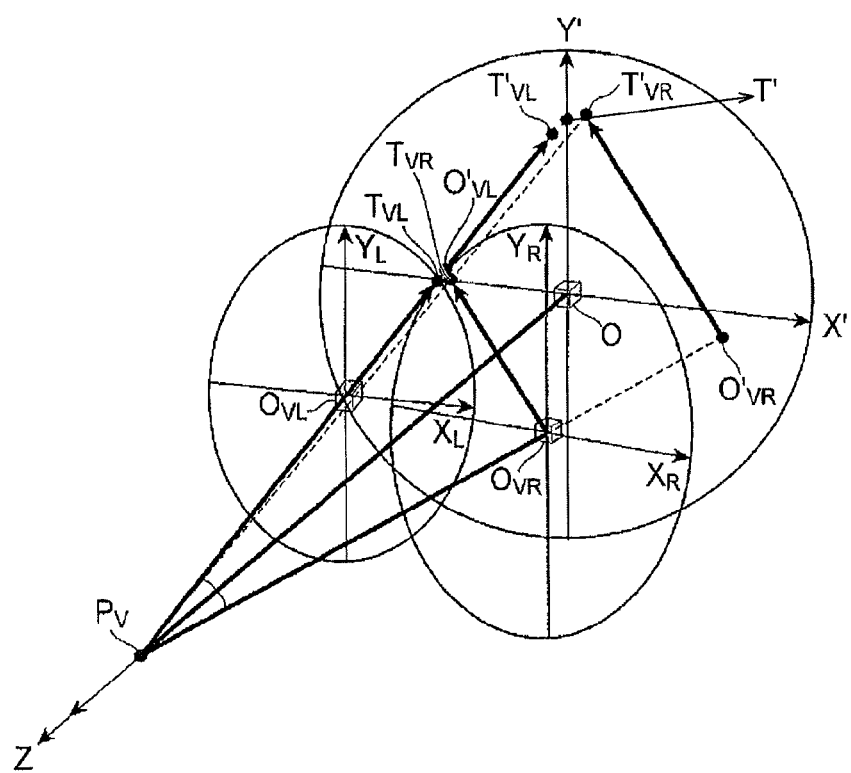
FIG. 5 is a diagram illustrating a gaze point detected by left and right stereo cameras of FIG. 1.

Specifically as illustrated in FIG. 5, by using the left and right stereo cameras 2a, 2b, the image processor 7 determines gaze points $T_{VL}$, $T_{VR}$ on their virtual gaze point planes $X_L$-$Y_L$, $X_R$-$Y_R$ from one pupil $P_V$. Subsequently, the image processor 7 projects the two gaze points $T_{VL}$, $T_{VR}$ and the origins $O_{VL}$, $O_{VR}$ of the virtual gaze point planes onto points $T'_{VL}$, $T'_{VR}$ and origins $O'_{VL}$, $O'_{VR}$ on the projective virtual gaze point plane X'-Y', respectively. Then, the image processor 7 calculates the distance $|T'_{VL}T'_{VR}|$ between the two gaze points on the projective virtual gaze point plane. Here, the projective virtual gaze point plane X'-Y' is a plane perpendicular to a bisector of an angle $O_{VL}P_VO_{VR}$ formed by lines connecting the origins $O_{VL}$, $O_{VR}$ of the two virtual gaze point planes and the pupil $P_V$, in which the distance from the pupil $P_V$ is set to the sum of distances from the pupil $P_V$ to the two virtual gaze point planes. However, the projective virtual gaze point plane X'-Y' is not limited to the plane perpendicular to the bisector of the angle $O_{VL}P_VO_{VR}$ as long as it is a plane having an average gradient with respect to the gradients of the two virtual gaze point planes $X_L$-$Y_L$, $X_R$-$Y_R$ and respective intersection angles therewith which become smaller at the same time, while its distance from the pupil $P_V$ may be set to any length.

Next, the image processor 7 corrects the coefficient k by performing a binary search from the initial value $k_0$. Specifically, it changes the coefficient k by adding an additional value to the initial value $k_0$, calculates the distance $|T'_{VL}T'_{VR}|$ between the two gaze points on the projective virtual gaze point plane each time, and searches for the coefficient k at which the distance $|T'_{VL}T'_{VR}|$ is the smallest. This corrects the coefficient k such that the two gaze points determined by the two cameras 2a, 2b are closer to each other on a predetermined plane, whereby the line of sight vectors calculated by using the two cameras 2a, 2b have directions closer to each other.

Using thus obtained coefficient k, the image processor 7 determines a line of sight vector of the subject A at a desirable timing and obtains an intersection between the line of sight vector and the display screen of the display device 8, thereby detecting a final gaze point Q of the subject A (gaze point detection step). Specifically, the image processor 7 takes a midpoint T' between the two gaze points $T'_{VL}$, $T'_{VR}$ determined by using the calibrated coefficient k as a gaze point on the projective virtual gaze point plane, and a vector PT' connecting the pupil center P and the gaze point T' as a line of sight vector. Next, the image processor 7 computes an intersection between the line of sight vector PT' and a plane along the display screen as a gaze point Q. The gaze point Q may also be detected on a predetermined plane other than the display screen. Thereafter, the image processor 7 displays the calculated gaze point Q with a marker on the display screen.

The foregoing is the gaze point detection procedure by the image processor 7, to which the following calibration procedure may be added by the image processor 7 in order to increase the accuracy of the gaze point to be detected.

One-Point Calibration Procedure

For determining the angle θ of the line of sight vector PT of the subject A by using the above-mentioned expression (3), the distance |r| between the pupil center and the corneal reflection is assumed to become zero at the time when the subject A gazes at the apertures 9a, 9b of the cameras 2a, 2b. However, structures of human eyeballs are likely to inhibit the corneal reflection point and the pupil center from coinciding with each other when the subject A sees the cameras 2a, 2b. Therefore, the image processor 7 corrects the shift in the gaze point caused by this phenomenon.

That is, simultaneously with the binary search for the coefficient k by the automatic calibration method, the image processor 7 computes an origin correction amount for the gaze point. First, while causing the display screen to display one target point (specified point) at a given position thereon and making the subject A gaze at the target point, the image processor detects the gaze point T' on the projective virtual gaze point plane. Subsequently, it computes the difference between thus detected gaze point T' and a point at which the coordinates of the target are projected onto the projective virtual gaze point plane as a correction amount ΔQ. By correcting each detected gaze point T' with the correction amount ΔQ, the image processor 7 can correct the detected gaze point Q by a shift corresponding to the error.

After detecting the gaze point while letting the subject A gaze at one target point, the image processor 7 may determine the value of the coefficient k by using the above-mentioned expression (3) and compute the correction amount ΔQ at the same time according to the positions of the gaze point and target.

Two-Point Calibration Procedure

By a two-point calibration procedure using two targets, the image processor 7 can correct the gaze point detection error caused by a nonlinear relationship between the distance |r| from the pupil center to the corneal reflection and the angle θ of the line of sight vector PT in addition to the origin correction of the gaze point.

More specifically, while letting the subject A gaze at a first target displayed at the center on the display screen, the image processor 7 initially determines the coefficient $k_1$ by a binary search (automatic calibration) and computes the origin correction amount ΔQ by the one-point calibration procedure.

Figure 6:
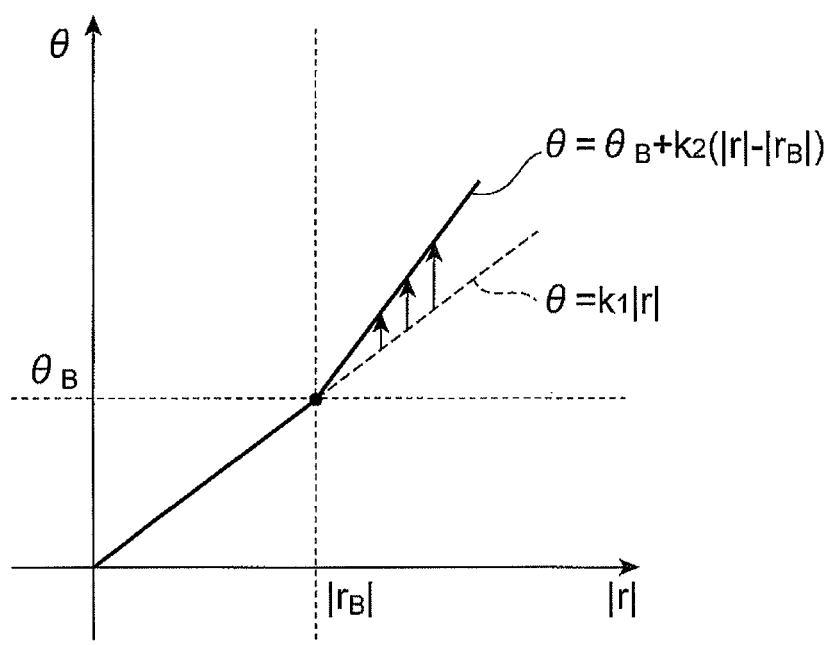
FIG. 6 is a graph illustrating a function $f_2$ for computing an angle of a line of sight vector set in an image processing unit of FIG. 1.

Here, the image processor 7 computes the angle θ of the line of sight vector PT by using the following expression (4):

[Math. 1]

$$\theta = f_2(|r|) = \begin{cases} k_1|r| & \text{if } k_1|r| < \theta_B \\ \theta_B + k_2(|r| - |r_B|) & \text{if } k_1|r| \geq \theta_B \end{cases} \quad (4)$$

in place of the above-mentioned expression (3). In the above-mentioned expression (4), $|r_B|$ and $\theta_B$ are the magnitude of the vector $|r|$ and angle θ detected when the first target point is displayed, respectively, and such a relationship that the change of the angle θ with respect to the change of the magnitude of vector $|r|$ varies from the point ($|r_B|$, $\theta_B$) acting as a base point is set, whereby the nonlinear component in their relationship when the angle θ is greater is taken into consideration (FIG. 6).

Next, while letting the subject A gaze at a second target displayed at the upper end in the center on the display screen, the image processor 7 detects the magnitude $|r_S|$ of the vector r at this time on the basis of the image data and computes a coefficient $k_2$ according to the following expression (5):

[Math. 2]

$$k_2 = \frac{\theta_S - \theta_B}{|r_S| - |r_B|} \quad (5)$$

by using an angle $\theta_S$ of the line of sight vector PT determined from a given target point. Subsequently, the image processor 7 corrects the function $f_2$ according to the determined coefficients $k_1$, $k_2$ and derives the angle θ of the line of sight vector PT from the vector r by using the corrected function $f_2$.

According to the gaze point detection device 1 and the gaze point detection method using the gaze point detection device 1 explained in the foregoing, face images of the subject A are produced as bright and dark pupil images by the two stereo cameras 2a, 2b and the light sources 3a, 3b on the outside of their apertures 9a, 9b, and the vectors r from the corneal reflection points of the subject to the pupils thereof are calculated from the respective face images and are applied to the functions $f_1$, $f_2$, so as to calculate the angles θ of the lines of sight of the subject A with respect to the reference lines. Further, the functions $f_1$, $f_2$ are corrected such that the respective directions of lines of sight calculated by using the two stereo cameras 2a, 2b are closer to each other, the directions of lines of sight are calculated by using the functions $f_1$, $f_2$, and then the gaze point Q on the display screen is detected according to the directions of lines of sight. This automatically corrects the functions $f_1$, $f_2$ for computing the line of sight directions without the subject recognizing it and thus enables high-precision gaze point detection while reducing the burden on the subject A.

Since the vectors r on planes which are perpendicular to reference lines of the two stereo cameras 2a, 2b while including three-dimensional coordinates of the pupils are calculated according to respective face images obtained by the two stereo cameras 2a, 2b, the gaze point detection device 1 can more accurately calculate the angle θ of lines of sight according to the pupil positions and corneal reflection points of the subject A.

The gaze point detection device 1 determines intersections of lines of sight with the virtual gaze point planes corresponding to the two stereo cameras 2a, 2b, projects the two intersections onto a predetermined projective virtual gaze point plane, and then corrects the functions $f_1$, $f_2$ such that the two intersections are closer to each other on the predetermined projective virtual gaze point plane. This makes it possible to evaluate the distance between the two projected points such that the directions of lines of sight detected by the two stereo cameras 2a, 2b are closer to each other, so as to correct the functions $f_1$, $f_2$.

The gaze point detection device 1 uses the function $f_1$ for detecting the line of sight direction from the vector r and thus simplifies the process for correcting the function $f_1$, thereby enabling immediate high-precision gaze point detection.

The gaze point detection device 1 makes it possible to add the one-point calibration procedure and thus can further correct the deviation in gaze point detection caused by human eyeball structures when the automatic calibration is performed alone.

The gaze point detection device 1 also makes it possible to add the two-point calibration procedure and thus can correct the function $f_1$ by using the function $f_2$ while taking account of the case where the vector r and the line of sight angle θ exhibit a nonlinear relationship therebetween, thereby achieving high-precision gaze point detection even when the line of sight has a larger angle with respect to the reference line of the camera.

The present invention is not limited to the above-mentioned embodiment. For example, the function f used for detecting the angle θ of the line of sight from the vector r connecting the corneal reflection point and the pupil center can be substituted by various functions in the gaze point detection method of the present invention.

For instance, the gaze point detection method in accordance with a modified example of the present invention may determine the function f as follows:

The image processor 7 determines the midpoint T' from the two gaze points T'$_{VL}$, T'$_{VR}$ detected by the left and right stereo cameras 2a, 2b by using the above-mentioned automatic calibration procedure. Then, the image processor 7 determines vectors T$_1$, T$_2$ directed from the projected points O'$_{VL}$, O'$_{VR}$ on the projective virtual gaze point plane (FIG. 5) to the midpoint T'.

Next, the image processor 7 determines the respective values of coefficient k by using the following expressions (6) and (7):

$$k = g_1^{-1}(|T_1|)/|r_1|, \quad (6)$$

$$k = g_1^{-1}(|T_2|)/|r_2|, \quad (7)$$

Here, $|r_1|$ and $|r_2|$ are the respective magnitudes of vectors r detected by the cameras 2a, 2b, $g_1$ is a mapping function from the virtual gaze point plane of each camera to the projective virtual gaze point plane, and $g_1^{-1}$ is its inverse mapping function. The image processor 7 thus acquires two k values when detecting one gaze point. Since the midpoint T' seems to be near the actual gaze point position, by repeating such a process and thereby changing the gaze point of the subject A, the image processor 7 can obtain values of the coefficient k in states where the magnitudes of $|r|$ changes variously.

Thereafter, the image processor 7 assumes that the function for calculating the angle θ from vector r from a corneal reflection point to a pupil center is given by the following expression (8):

$$\theta = f_3(|r|) = k(|r|) \times |r| \quad (8)$$

as an unknown function in which the coefficient k changes according to the magnitude $|r|$ of vector r. Then, by regression with a nonlinear function using the values of coefficient k obtained for various values of |r| according to the above-mentioned method, the image processor 7 determines the function k(|r|) as a polynomial or any other appropriate nonlinear form in which |r| is a variable. The image processor 7 further detects the two gaze points $T'_{VL}$, $T'_{VR}$ according to the expression (8) by using the left and right stereo cameras 2a, 2b. This allows the image processor 7 to accurately compute the gaze point Q on the display screen while taking account of the nonlinear relationship between the vector r and the angle θ.

Though the image processor 7 measures three-dimensional coordinates of pupils of the subject A by using the stereo method according to the image data obtained by the stereo cameras 2a, 2b, three-dimensional coordinates of pupils may be computed by using distance information issued from an optical time-of-flight range image sensor used as a camera as described in Japanese Patent Application Laid-Open No. 2005-230049.

Digital cameras such as CCD cameras and CMOS cameras may also be used as the stereo cameras 2a, 2b.

The gaze point detection device 1 may be equipped with three or more cameras and their corresponding light sources in place of the two stereo cameras 2a, 2b. In this case, the gaze point detection device 1 may operate so as to correct functions for detecting line of sight directions corresponding to the respective cameras such that the line of sight directions calculated by the cameras are closer to each other.

Preferably, the invention in accordance with the above-mentioned aspect further comprises a pupil coordinate detection step of detecting three-dimensional coordinates of the pupil of the subject according to respective face images obtained by at least two cameras, while the vector calculation step calculates the vector r on a plane, perpendicular to the reference line of the camera, including the three-dimensional coordinates of the pupil. This can more accurately calculate the angle θ of the line of sight according to the pupil position and corneal reflection point of the subject.

Preferably, the parameter correction step determines intersections of the lines of sight with respective virtual gaze point planes including positions of at least two cameras and being perpendicular to the reference lines thereof, projects the intersections onto a predetermined projective virtual gaze point plane, and then corrects the function f such that the intersections are closer to each other on the projective virtual gaze point plane. This makes it possible to evaluate the distance between the two projected points and correct the function f such that the directions of lines of sight detected by at least two cameras are closer to each other.

Preferably, the line of sight direction calculation step calculates the angle θ of the line of sight of the subject according to the following expression (2):

$$\theta = k \times |r| \quad (2)$$

by using a parameter k, and the parameter correction step corrects the parameter k. Employing such a structure simplifies the process for correcting the function f, thereby enabling immediate high-precision gaze point detection.

Preferably, the parameter correction step changes the gaze point of the subject, so as to compute the parameter k when the vector r is changed variously, thereby determining the parameter k as a function of the magnitude |r| of vector r, and the gaze point detection step calculates the direction of the line of sight by using the function and the expression (2). This can detect the line of sight direction highly accurately even when the line of sight direction deviates greatly from the optical axis of the camera.

Preferably, the gaze point detection step detects the gaze point occurring when the subject is caused to gaze at one specified point on the predetermined plane and corrects an intersection of the line of sight with the predetermined plane according to a deviation between the specified point and the gaze point. This can further correct the deviation in gaze point detection occurred only by the automatic calibration.

Preferably, the gaze point detection step detects the respective gaze points occurring when the subject is caused to gaze at two or more specified points on the predetermined plane, and the parameter correction step further corrects the function f according to a deviation between the specified point and the gaze point. This makes it possible to correct the function f while taking account of the case where the vector r and the angle θ exhibit a nonlinear relationship therebetween, thus achieving higher-precision gaze point detection.

Preferably, the vector calculation step detects a pupil position of the subject by taking a difference between the bright and dark pupil images. Employing such a structure can easily detect the pupil position of the subject.

INDUSTRIAL APPLICABILITY

The present invention is used for a gaze point detection method and a gaze point detection device and enables high-precision gaze point detection, while reducing the burden on a test subject, no matter who the subject is.

REFERENCE SIGNS LIST

1 . . . gaze point detection device; 2a, 2b . . . stereo camera; 3a, 3b . . . light source; 4 . . . light emission circuit (control circuit); 5 . . . synchronization signal generator (control circuit); 6 . . . delay circuit (control circuit); 7 . . . image processor (image processing unit); 8 . . . display device (predetermined plane); 9a, 9b . . . aperture; A . . . subject; G . . . corneal reflection point; P . . . pupil center; OP . . . reference line; PT . . . line of sight; Q . . . gaze point; θ . . . line of sight angle

The invention claimed is:

1. A gaze point detection method comprising:
a face image production step of producing a face image of a subject as a bright pupil image and a dark pupil image by using at least two cameras and a light source disposed on the outside of apertures of the at least two cameras;
a vector calculation step of calculating a vector r from a corneal reflection point of the subject to a pupil thereof on a plane perpendicular to a reference line connecting the camera and the pupil according to the face image obtained by each of the at least two cameras;
a line of sight direction calculation step of calculating respective angles θ of lines of sight of the subject with respect to the reference lines of the at least two cameras according to the vectors r corresponding to the at least two cameras from the following expression (1):

$$\theta = f(|r|) \quad (1)$$

by using a function f;
a parameter correction step of correcting the function f such that at least two gaze points on a predetermined plane determined by the directions of lines of sight calculated so as to correspond to the at least two cameras are closer to each other; and
a gaze point detection step of calculating the directions of lines of sight according to the expression (1) by using the function f corrected by the parameter correction step and determining an intersection of the lines of sight on the predetermined plane, so as to detect a gaze point of the subject on the predetermined plane, wherein the parameter correction step determines intersections of the lines of sight with respective virtual gaze point planes including positions of at least two cameras and being perpendicular to the reference lines thereof, projects the intersections onto a predetermined projective virtual gaze point plane, and then corrects the function f such that the intersections are closer to each other on the projective virtual gaze point plane.

2. A gaze point detection method according to claim 1, further comprising a pupil coordinate detection step of detecting three-dimensional coordinates of the pupil of the subject according to respective face images obtained by the at least two cameras;

wherein the vector calculation step calculates the vector r on a plane, perpendicular to the reference line of the camera, including the three-dimensional coordinates of the pupil.

3. A gaze point detection method according to claim 1, wherein the line of sight direction calculation step calculates the angle θ of the line of sight of the subject according to the following expression (2):

$$\theta = k \times |r| \tag{2}$$

by using a parameter k; and wherein the parameter correction step corrects the parameter k.

4. A gaze point detection method according to claim 3, wherein the parameter correction step changes the gaze point of the subject, so as to compute the parameter k when the vector r is changed variously, thereby determining the parameter k as a function of the magnitude |r| of vector r; and wherein the gaze point detection step calculates the direction of the line of sight by using the function and the expression (2).

5. A gaze point detection method according to claim 1, wherein the gaze point detection step detects the gaze point occurring when the subject is caused to gaze at one specified point on the predetermined plane and corrects an intersection of the line of sight with the predetermined plane according to a deviation between the specified point and the gaze point.

6. A gaze point detection method according to claim 1, wherein the gaze point detection step detects the respective gaze points occurring when the subject is caused to gaze at two or more specified points on the predetermined plane; and wherein the parameter correction step further corrects the function f according to a deviation between the specified point and the gaze point.

7. A gaze point detection method according to claim 1, wherein the vector calculation step detects a pupil position of the subject by taking a difference between the bright and dark pupil images.

8. A gaze point detection device for detecting a gaze point of a subject on a predetermined plane according to a face image of the subject, the device comprising:

at least two cameras for acquiring the face image of the subject;

a light source disposed on the outside of apertures of the at least two cameras;

a control circuit for controlling the cameras and light source; and an image processing unit for processing image signals issued from the at least two cameras;

wherein the control circuit performs such control as to produce the face image of the subject as a bright pupil image and a dark pupil image;

wherein the image processing unit calculates a vector r from a corneal reflection point of the subject to a pupil thereof on a plane perpendicular to a reference line connecting the camera and the pupil according to the face image obtained by each of the at least two cameras, calculates respective angles θ of lines of sight of the subject with respect to the reference lines of the at least two cameras according to the vectors r corresponding to the at least two cameras from the following expression (1):

$$\theta = f(|r|) \tag{1}$$

by using a function f, corrects the function f such that at least two gaze points on a predetermined plane determined by the directions of lines of sight calculated so as to correspond to the at least two cameras are closer to each other, and calculates the directions of lines of sight according to the expression (1) by using the corrected function f and determines an intersection of the lines of sight on the predetermined plane, so as to detect a gaze point of the subject on the predetermined plan;

wherein the image processing unit determines intersections of the lines of sight with respective virtual gaze point planes including positions of the at least two cameras and being perpendicular to the reference lines thereof, projects the intersections onto a predetermined projective virtual gaze point plane, and then corrects the function f such that the intersections are closer to each other on the projective virtual gaze point plane.

* * * * *